(12) United States Patent
Stautner et al.

(10) Patent No.: US 10,481,222 B2
(45) Date of Patent: Nov. 19, 2019

(54) FLUID PATH INSERT FOR A CRYOGENIC COOLING SYSTEM

(71) Applicant: General Electric Company, Schenectady, NY (US)

(72) Inventors: Ernst Wolfgang Stautner, Niskayuna, NY (US); Jan Henrik Ardenkjaer-Larsen, Broendby (DK); Patrick L. Padgett, Detroit, MI (US); Jonathan Alan Murray, Waukesha, WI (US); Rui Chen, Clifton Park, NY (US); James Richard Trigger, Rotterdam Junction, NY (US); Arnaud Comment, Cambridge (GB); Albert Po-Fu Chen, Toronto (CA)

(73) Assignee: General Electric Company, Schenectady, NY (US)

(*) Notice: Subject to any disclaimer, the term of this patent is extended or adjusted under 35 U.S.C. 154(b) by 178 days.

(21) Appl. No.: 15/658,123

(22) Filed: Jul. 24, 2017

(65) Prior Publication Data
US 2019/0025387 A1    Jan. 24, 2019

(51) Int. Cl.
| | | |
|---|---|---|
| G01R 33/31 | (2006.01) |
| F25B 19/00 | (2006.01) |
| F25D 19/00 | (2006.01) |
| G01R 33/28 | (2006.01) |
| F25D 29/00 | (2006.01) |

(Continued)

(52) U.S. Cl.
CPC ............ *G01R 33/31* (2013.01); *F25B 19/005* (2013.01); *F25D 19/006* (2013.01); *F25D 21/002* (2013.01); *F25D 29/001* (2013.01); *G01N 1/42* (2013.01); *G01R 33/282* (2013.01)

(58) Field of Classification Search
CPC .... F25D 19/006; F25D 21/002; F25D 29/001; F25B 19/005; G01N 1/42; G01R 33/31; G01R 33/282
See application file for complete search history.

(56) References Cited

U.S. PATENT DOCUMENTS 5,235,817 A * 8/1993 Gallagher ............. F17C 13/006
                                                      250/352
5,274,237 A * 12/1993 Gallagher ................. G01T 1/00
                                                      250/370.15

(Continued)

OTHER PUBLICATIONS

Archer, J.W.; "Multiple Mixer, Cryogenic Receiver for 200-350 GHz", Review of Scientific Instruments, vol. 54, Issue 10, http://aip.scitation.org/doi/pdf/10.1063/1.1137247, Jun. 1998.

(Continued)

*Primary Examiner* — David J Bolduc

(57) ABSTRACT

A cooling system is provided. The cooling system is associated with a dynamic nuclear polarization system and configured to cool a sample to a temperature suitable for dynamic nuclear polarization to be carried out on the sample while the sample is in the cooling system. The cooling system includes a cryogenic chamber that includes a cryogenic fluid. The cooling system also includes a removable sample sleeve insertable within a portion of the cryogenic chamber. The removable sample sleeve is configured to define a sample path for the sample within the cryogenic chamber that is isolated from other parts of the cooling system.

19 Claims, 9 Drawing Sheets

(51) Int. Cl.
*F25D 21/00* (2006.01)
*G01N 1/42* (2006.01)

(56) References Cited

U.S. PATENT DOCUMENTS

| | | | | |
|---|---|---|---|---|
| 6,079,213 | A * | 6/2000 | Driehuys | A61K 49/1815 62/3.1 |
| 7,631,507 | B2 | 12/2009 | Stautner | |
| 7,633,290 | B1 | 12/2009 | Al-Khalidy et al. | |
| 8,731,640 | B2 | 5/2014 | Urbahn et al. | |
| 2002/0094317 | A1 * | 7/2002 | Pines | A61K 49/1815 424/9.3 |
| 2002/0147396 | A1 * | 10/2002 | Fleury | G01R 33/31 600/410 |
| 2004/0049108 | A1 * | 3/2004 | Ardenkjaer-Larsen | G01R 33/282 600/412 |
| 2004/0066193 | A1 * | 4/2004 | Ardenkjaer-Larsen | G01R 33/282 324/309 |
| 2005/0225328 | A1 * | 10/2005 | Ardenkjaer-Larsen | G01R 33/282 324/321 |
| 2006/0199272 | A1 * | 9/2006 | Wistrand | G01R 33/282 436/173 |
| 2007/0038076 | A1 * | 2/2007 | Osada | G01R 33/282 600/420 |
| 2008/0100293 | A1 * | 5/2008 | Lucas | G01R 33/282 324/307 |
| 2008/0104966 | A1 | 5/2008 | Stautner | |
| 2008/0229928 | A1 | 9/2008 | Urbahn et al. | |
| 2008/0240998 | A1 | 10/2008 | Urbahn et al. | |
| 2008/0242974 | A1 | 10/2008 | Urbahn et al. | |
| 2010/0251732 | A1 * | 10/2010 | Leach | G01R 33/282 62/51.1 |
| 2011/0036453 | A1 * | 2/2011 | Ardenkjaer-Larsen | B01F 1/0022 141/311 R |
| 2011/0062392 | A1 * | 3/2011 | Kalechofsky | A61K 49/10 252/582 |
| 2011/0095759 | A1 * | 4/2011 | Bhattacharya | A61B 5/055 324/307 |
| 2011/0150706 | A1 * | 6/2011 | Murphy | G01R 33/282 422/105 |
| 2012/0007599 | A1 * | 1/2012 | Prestegard | G01N 1/42 324/309 |
| 2012/0117985 | A1 * | 5/2012 | Urbahn | G01N 13/00 62/45.1 |
| 2013/0047633 | A1 | 2/2013 | Leach et al. | |
| 2014/0123681 | A1 | 5/2014 | Urbahn et al. | |
| 2014/0223923 | A1 * | 8/2014 | Kalechofsky | A61K 49/10 62/3.1 |
| 2015/0084632 | A1 * | 3/2015 | Wilhelm | G01R 33/282 324/318 |
| 2015/0168079 | A1 | 6/2015 | Stautner et al. | |
| 2019/0003653 | A1 * | 1/2019 | Stautner | F17C 13/06 |

OTHER PUBLICATIONS

Demikhov, E., et al.; "8 T Cryogen Free Magnet With a Variable Temperature Insert Using a Heat Switch", IEEE Transactions on Applied Superconductivity, vol. 20, Issue 3, pp. 612-615, Jun. 2010.

Dietrich, M., et al.; "A Compact Thermal Heat Switch for Cryogenic Space Applications Operating Near 100 K", Cryogenics, vol. 59, pp. 70-75, http://www.sciencedirect.com/science/article/pii/S001122751300115X, Jan.-Feb. 2014.

Federspiel, Marianne, et al.; "Production of Hyperpolarized 13C-Pyruvate by Dissolution Dynamic Nuclear Polarization", The Journal of Nuclear Medicine, vol. 57, No. 2, http://jnm.snmjournals.org/content/57/supplement_2/2639.short, May 1, 2016.

* cited by examiner

FLUID PATH INSERT FOR A CRYOGENIC COOLING SYSTEM

BACKGROUND

The subject matter disclosed herein relates to dynamic nuclear polarization systems.

Dynamic nuclear polarization (DNP) is a technique that is used to generate an excess of a nuclear spin orientation relative to another spin orientation, which is sometimes referred to as hyperpolarization. The excess of one spin orientation over another is reflected by an increase in the signal-to-noise ratio of measurements in nuclear magnetic resonance systems such as magnetic resonance imaging (MRI) systems.

DNP often involves cooling samples to particularly low temperatures. For instance, DNP systems may include liquid cryogen (e.g., liquid helium) baths used to cool samples to very low temperatures, sometimes below four Kelvin. However, in some cases, icing within a sample path (e.g., a path within the DNP system between where a sample is first introduced to the DNP system and the liquid cryogen bath) may occur (e.g., due to a vial or syringe breaking). In some instances, ice may be removed by warming the entire DNP system, which results in system downtime and can increase operating costs.

BRIEF DESCRIPTION

In one embodiment, a cooling system is associated with a dynamic nuclear polarization system and configured to cool a sample to a temperature suitable for dynamic nuclear polarization to be carried out on the sample while the sample is in the cooling system. The cooling system includes a cryogenic chamber that includes a cryogenic fluid. The cooling system also includes a removable sample sleeve insertable within a portion of the cryogenic chamber. The removable sample sleeve is configured to define a sample path for the sample within the cryogenic chamber that is isolated from other parts of the cooling system.

In another embodiment, a removable sample sleeve is configured to be disposed within a cooling system of a dynamic nuclear polarization system and collect ice that forms within the cooling system. The removable sample sleeve includes an upper portion that is configured to be disposed within a portion of the cooling system outside of a sample pot of the cooling system. The removable sample sleeve also includes a lower portion configured to be disposed within the sample pot, wherein the lower portion comprises a thermal switch configured to warm the lower portion. Additionally, the removable sample sleeve includes a body portion configured to be disposed both within and outside of the sample pot.

In yet another embodiment, a controller-executable method of de-icing a removable insert sleeve of a cooling system includes receiving a first set of sensor data from one or more sensors configured to collect data regarding the cooling system. The cooling system is configured to cool a sample, and the cooling system includes a removable sample sleeve configured to collect ice that forms within the cooling system. The removable sample sleeve includes a thermal insert configured to directly heat a bottom surface of the removable sample sleeve. The method also includes determining whether the first set of sensor data is indicative of ice formation in the cooling system. Additionally, the method includes sending a command to actuate a thermal switch when the first set of sensor data is indicative of ice formation in the cooling system. Moreover, the method includes receiving a second set of sensor data from the one or more sensors and determining whether the second set of sensor data is indicative of de-icing conditions. Furthermore, the method includes sending a command to deactivate the thermal switch when the second set of sensor data is indicative of de-icing conditions.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

As set forth above, icing may sometimes occur in dynamic nuclear polarization (DNP) systems that utilize a cryogenic fluid (e.g., liquid helium) bath to cool samples to temperatures at or below approximately four Kelvin. To help the DNP system operate properly, the ice is typically removed by warming the system. Heating up the DNP system to remove ice may result in the inability to cool samples for extended periods of time (e.g., days or weeks). The present disclosure provides systems and methods that contain ice formation to a limited, removable, area of DNP systems. Moreover, the present disclosure provides systems and methods for de-icing specific portions of the DNP systems.

Figure 1:
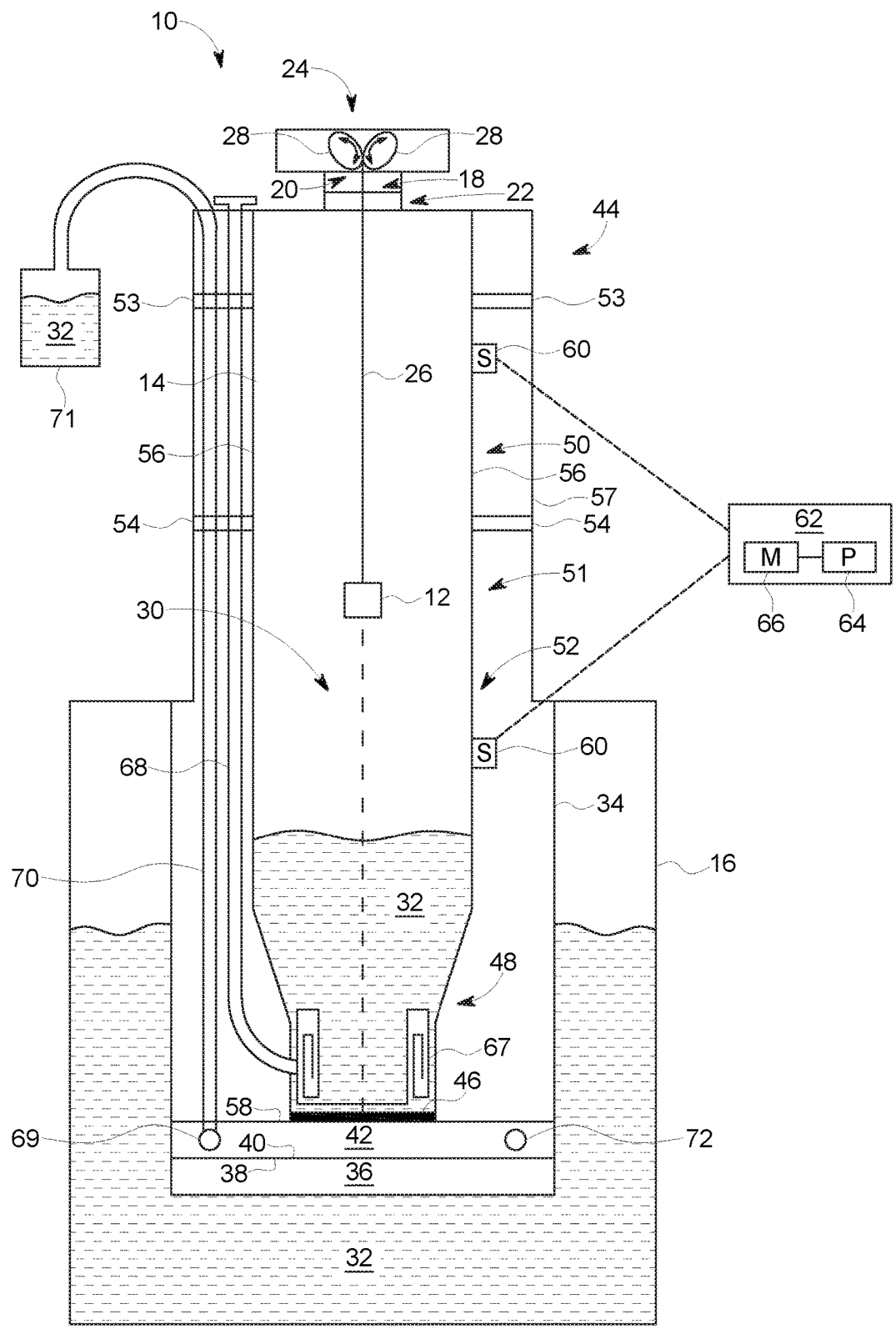
FIG. 1 is a schematic diagram of a cooling system that includes a removable sample sleeve, in accordance with present embodiments.

Keeping the foregoing in mind, FIG. 1 is a schematic diagram of a cooling system 10 used to cool one or more samples 12 that may be included in a storage container (e.g., a vial). The cooling system 10 may be included in a dynamic nuclear polarization (DNP) system. The sample 12 may include chemical compounds, solutions, and the like. For example, the sample 12 may include pyruvate, pyruvic acid, urea, uric acid, and/or glycerol. Moreover, as discussed in detail below, the cooling system 10 includes a removable sample sleeve 14 that may inhibit the formation or migration of ice within other areas of the cooling system 10. The removable sample sleeve 14 may also enable more rapid de-icing procedures for the cooling system 10 as compared to other configurations.

During operation of the system 10, the sample 12 may be cooled via a cryogenic chamber 16 (e.g., a liquid cryogen bath) into which the sample 12 may be placed. To facilitate transitioning the sample 12 from the room temperature environment into the cooling system 10, the cooling system 10 includes an airlock chamber 18 into which the sample 12 may be inserted. The airlock chamber 18 may be used to maintain the sample 12 at a suitable pressure. For instance, in some cases, the airlock chamber 18 may be utilized to keep the sample at a pressure that is lower than standard atmospheric pressure. The airlock chamber 18 may include a baffle 20 and gate valve 22 that aid in maintaining a certain pressure within the cooling system 10.

Moreover, the system may also include a positioning system 24 that may be used to move the sample 12 within the cooling system 10. For instance, the sample 12 may be coupled to a line 26 (e.g., a hollow tube), and the line 26 may be coupled to pitch wheels 28 of the positioning system 24. Rotation of the pitch wheels 28 causes the sample 12 to be moved along a sample path 30 toward and away from the cryogenic chamber 16.

The sample 12 may be cooled within the cooling system 10 via convection and conduction. For example, as the sample 12 is moved closer to the cryogenic chamber 16 but not placed in a cryogenic fluid 32 (e.g., liquid helium), the cooling may occur by way of convection, and the sample 12 may be placed within the cryogenic fluid 32 to be cooled via conduction.

In addition to the cryogen fluid 32, the cryogenic chamber 16 includes a sample pot 34 and a cooling plate 36. The sample pot 34 forms an enclosed volume within the cryogenic chamber 16. The sample pot 34 may be thermally insulated so as to maintain a constant temperature within the sample pot 34. By way of non-limiting example, in certain embodiments, the temperature in the sample pot 34 is less than 1 Kelvin. More specifically, in certain embodiments the temperature in the sample pot 34 is between about 0.75 K and 0.95 K. Moreover, a portion of the sample pot 34 may directly contact the cryogenic fluid 32 that is stored within the cryogenic chamber 16.

The cooling plate 36 aids in cooling the sample pot 34. The cooling plate 36 may be the bottom surface of the sample pot 34 and/or form the bottom of the sample pot 34. That is, the cooling plate 36 may not be a separate component that inserted into the sample pot 34. As illustrated, the cooling plate 36 may be disposed within cryogenic fluid 32 of the cryogenic chamber 16 such that all but one surface of the cooling plate 36 are surrounded by the cryogenic fluid 32. An upper surface 38 of the cooling plate 36 contacts a lower surface 40 of a thermal switch 42 configured to contact the removable sample sleeve 14. The cooling plate 36 may also cool the thermal switch 42. That is, the cooling plate 36 may be used to remove heat from the thermal switch 42.

Turning the discussion now to the removable sample sleeve 14, the removable sample sleeve 14 may be positionable within the cooling system 10. More specifically, the removable sample sleeve 14 may be disposed within an upper portion 44 of the cooling system 10 as well as the sample pot 34 of the cryogenic chamber 16. In other words, the removable sample sleeve 14 has a geometry and size appropriate for the cooling system 10. The removable sample sleeve 14 may be made from various metals and metal alloys. For instance, the removable sample sleeve may be made from nickel-chromium based alloys (e.g., Inconel®), stainless steel, aluminum, titanium, titanium-aluminum alloys, and/or any combination thereof. Additionally, a bottom surface 46 of a lower portion 48 of the removable sample sleeve 14 may be copper-plated, gold-plated, or copper and gold-plated.

The removable sample sleeve 14 includes a body portion 50, and the lower portion 48 that is in thermal communication with the thermal switch 42. That is, as illustrated, the lower portion 48 of the removable sample sleeve 14 may be positioned within the sample pot 34, while an upper portion 51 of the body portion 50 protrudes out of the sample pot. In some embodiments, the upper portion 51 may form a seal at a transition point 52 between the upper portion 51 and lower portion 48 of the removable sample sleeve 14. For instance, formation of a seal at the transition point 52 may be achieved via an attachment that may be coupled to the removable sample sleeve 14. Additionally, the body portion 50 include a portion of the upper portion 51 and lower portion 48. For instance, the upper portion 51 may be a portion the body portion 50 that is positioned outside of the sample pot 34, while the lower portion 48 may include a portion of the body portion 50 that is located within the sample pot 34.

The removable sample sleeve 14 defines the sample path 30 within the cooling system 10, and the sample path 30 is isolated from other parts of the cooling system 10, such as the cryogenic fluid 32 in the cryogenic chamber 16 that is outside of the sample pot 34. As illustrated, the sample path 30 extends through the upper portion 51, body portion 50 and lower portion 48 of the removable sample sleeve 14. That is, the sample 12 may be raised and lowered (e.g. via the positioning system 24) within the removable sample sleeve 14. Additionally, the lower portion 48 includes a certain amount of the cryogenic fluid 32 separate from the cryogenic fluid 32 in the cryogenic chamber 16 outside of the sample pot 34. The sample 12 may be moved into the cryogenic fluid 32 contained in the lower portion 48 to conductively cool the sample 12.

The removable sample sleeve 14 may be secured in place via a first set of links 53 and a second set of links 54. More specifically, the first set of link 53 and the second set of links 54 may include beryllium copper springs or fingerstock, and the first set of links 53 and second set of link 54 may physically and thermally connect walls 56 of the removable sample sleeve 14 to an outer tube 57 that surrounds the removable sample sleeve 14. Due to the first and second sets of links 53, 54, the walls 56 and outer tube 57 may be equivalent in temperature. Additionally, the first set of link 53 and second set of link 54 may be maintained at a constant temperature by a cryocooler.

Generally, the temperature within the cooling system 10 is lower in areas closer to, and within, the cryogenic chamber 16. For example, the temperature in the area of the cooling system 10 between the gate valve 22 and the first set of links 53 is generally about 40 K or warmer. The temperature in the area between the first set of links 53 and the second set of links 54 generally ranges from about 4 K to 40 K. And, as discussed above, the temperature in the sample pot 34, in which the lower portion 48 of the removable sample sleeve 14 is positioned, may be less than about 1 K. That is, as the sample 12 is lowered along the sample path 30 towards and into the sample pot 34, the sample becomes subjected to lower and lower temperatures.

In some instances, such as when a container of the sample 12 is lowered too quickly into the sample pot 34, the container of the sample 12 may mechanically fail. For instance, a container of the sample 12 include a vial, syringe, or some other form of encasement which may break, causing the contents of the sample 12 to disperse within the cooling system 10. However, such a dispersion of the sample 12 is limited to occurring within the removable sample sleeve 14. In other words, the removable sample sleeve 14 prohibits the sample 12 from entering any portion of the cooling system 10 that is outside of the removable sample sleeve 14, which reduces or eliminates the likelihood of ice or other materials contaminating the sample pot 34.

While mechanical failure (e.g., breakage) of the container of the sample 12 is one potential source of ice formation (e.g., on walls 56 of the removable sample sleeve 14), ice can form within the cooling system 10 for various other reasons. For instance, exposure of interior portions of the cooling system 10 to the ambient environment, which includes water vapor, may cause ice to form as the water vapor condenses first to water then freezes to produce ice. In accordance with present embodiments, because the removable sample sleeve 14 is positioned within the cooling system 10 at an interface between the external environment and the interior of the cooling system 10, the removable sample sleeve 14 collects ice that may potentially form as a result of water vapor infiltration (e.g., from sample introduction). That is, the removable sample sleeve 14 limits the occurrence of ice to its internal area.

Ice may be removed from the cooling system 14 in a number of ways. As described above, ice formation may be limited to occurring within the removable sample sleeve 14. Thus, the removable sample sleeve 14 may be removed from the cooling system 10, and ice that has formed may subsequently be removed from the removable sample sleeve 14. However, ice may also be removed from the removable sample sleeve 14 without taking the removable sample sleeve 14 out of the cooling system 10. For example, the thermal switch 42 may be used to de-ice the removable sleeve 14.

In the illustrated configuration, for example, the thermal switch 42 may heat the bottom surface 46 of the removable sample sleeve 14. More specifically, the thermal switch 42 may become heated in response to an applied stimulus (e.g., electrical signal, or gas flow through the thermal switch 42), and the generated heat may be transferred from a top surface 58 of the thermal switch 42 to the bottom surface 46 of the lower portion 48 of the removable sample sleeve 14 (e.g., via conduction). Heat may transfer at least into the lower portion 48, causing de-icing to occur within the removable sample sleeve 14. For instance, the thermal switch 42 may heat the bottom surface 46 of the removable sample sleeve 14 to a temperature that is sufficient to cause melting and vaporization of the ice in the removable sample sleeve, and at a reduced internal pressure of the cooling system 10. By way of non-limiting example, the thermal switch 42 may heat at least the lower portion 48 of the removable sample sleeve 14 to between about 290 K and 300 K. The particular temperature to which the removable sample sleeve 14 is heated may depend on a number of factors, some or all of which may be monitored as described herein. For instance, the temperature to which the removable sample sleeve 14 is heated may depend on the amount of ice present within the removable sample sleeve 14, the pressure within the removable sample sleeve 14, the heating capability of the thermal switch 42, or any combination of these and/or other factors.

During de-icing, cryogenic fluid 32 within the thermal switch 42 evaporates and may enter the external source 71 of cryogenic fluid 32. Likewise, as the temperature within the removable sample sleeve 14 increases, the cryogenic fluid 32 within the removable sample sleeve 32 evaporates. Upon switching off the heater of the thermal switch 42, the cryogenic fluid 32 is reclaimed from the external source 71 and enters the thermal switch 42 where the cryogenic fluid 42 may condense into liquid form. As such, the cryogenic fluid 32 in the thermal switch 42 is maintained within the cooling system 10 before, during, and after de-icing.

Furthermore, it should also be noted that the thermal switch 42 is removably attached to the bottom surface 46 of the removable sample sleeve 14. Moreover, while the top surface 58 of the thermal switch 42 is larger than the bottom surface 46 of the removable sample sleeve 14 in the illustrated embodiment, heating may be limited to an area of the top surface 58 that directly contacts the bottom surface 46. Similarly, in other embodiments, a dimension (e.g., a length or width), or a surface area, of the top surface 58 may be substantially the same as or smaller than a corresponding dimension or surface area of the bottom surface 46 of the removable sample sleeve 14.

Inclusion of the removable sample sleeve 14 in the cooling system 10 enables ice to be removed from the cooling system 10 without heating the entire cooling system 10. Indeed, as explained above, ice may be removed by heating a portion of the cooling system 10 (e.g., heating the bottom surface 46 via the thermal switch 42). Further, the cold plate 36 serves as a thermal barrier between the thermal switch 42 and the surrounding sample pot 34 and cryogenic fluid 32, which limits heating of the sample pot 34 and the cryogenic fluid 32 by the thermal switch 42 during de-icing procedures.

As noted, in addition to or as an alternative to heating the removable sample sleeve 14 within the cooling system 10, the removable sample sleeve 14 may be removed from the cooling system 10 and cleaned to remove ice. De-icing, either via heating provided by the thermal switch 42 or removal of the removable sample sleeve 14, may be completed in less than one hour as compared to traditional de-icing procedures which can potentially cause downtime for 24 hours, three days, or longer. Indeed, de-icing occur without depowering the NMR coil 67. After de-icing, the cooling of samples 12 may be resumed in under twelve hours, and, in some cases, cooling may be resumed in less than one hour (e.g., one hour or less in total between de-icing and resuming cooling of the sample 12). The time that passes before cooling may resume typically depends on the temperature in the sample pot 34. For example, if the thermal switch 46 is actuated, causing the bottom surface 46 of the removable sample sleeve 14 to be warmed, the temperature within the sample pot 34 can potentially rise above temperatures suitable for cooling samples 12. That is, the temperature within the sample pot 34 may become greater than 1 Kelvin. To the extent that the temperature within the sample pot 34 has risen during a de-icing procedure, once the thermal switch 42 is deactivated, the sample pot 34 may re-cool to a temperature that is suitable for cooling samples (e.g., about 0.75 to 0.95 K), and cooling of samples 12 may be resumed.

As set forth above, the introduction of the samples 12, warming using the thermal switch 42, and similar procedures may be controlled and adjusted in response to certain detected parameters of the cooling system 10. To provide for such control, in some embodiments, the cooling system 10 may include one or more sensors 60 that detect various properties of the cooling system 10 such as temperature, pressure, and a status of the sample 12 (e.g., location within the cooling system 10 and/or whether the sample has broken). In the illustrated embodiment, the sensors 60 are communicatively coupled to a controller 62 that includes a processor 64 and memory 66. The memory 66 may include instructions that may be accessed and executed by the processor 64. By way of non-limiting example, the memory 66 may include instructions that, when executed by the processor 64, cause the controller 62 to actuate the thermal switch 42. For example, when certain values of temperature, pressure, or both of temperature and pressure are detected by the sensors 60, the processor 64 may evaluate such temperatures and/or pressures and cause actuation of the thermal switch 42 in response to determining that a de-icing procedure is appropriate. As another example, the sensors 60 may provide feedback to the controller 62 that is indicative of mechanical failure of a container of the sample 12, and the processor 64 may cause removal of the sample 12 from the removable sample sleeve 14, actuation of the thermal switch 42, or similar actions.

As noted above, the cooling system 10 may be for DNP applications. In some embodiments, the cooling system may include components used to perform DNP. For example, in the illustrated embodiment, the cooling system 10 includes nuclear magnetic resonance (NMR) coils 67 and a waveguide 68. The sample 12 may be placed within the NMR coil 67, and data regarding the sample 12 may be collected. More specifically, electromagnetic radiation (e.g., microwaves) produced by the NMR coil 67 is directed onto the sample 12 and may be received by the NMR coil 67. The waveguide 68 may be used to guide the electromagnetic radiation to and/or from the NMR coils 67.

It should also be noted that the thermal switch 42 may aid in the cooling of the sample pot 34 and/or the removable sample sleeve 14. For example, the thermal switch 42 may receive cooling fluid (e.g., the cryogenic fluid 32) via an inlet 69 (e.g., that receives cryogenic fluid 32 from the cryogenic chamber 16 or is connected to a tube 70 that is coupled to an external source 71 of cryogenic fluid), the cooling fluid may be circulated within the thermal switch 42 before exiting the thermal switch 42 via an outlet 72.

Figure 2:
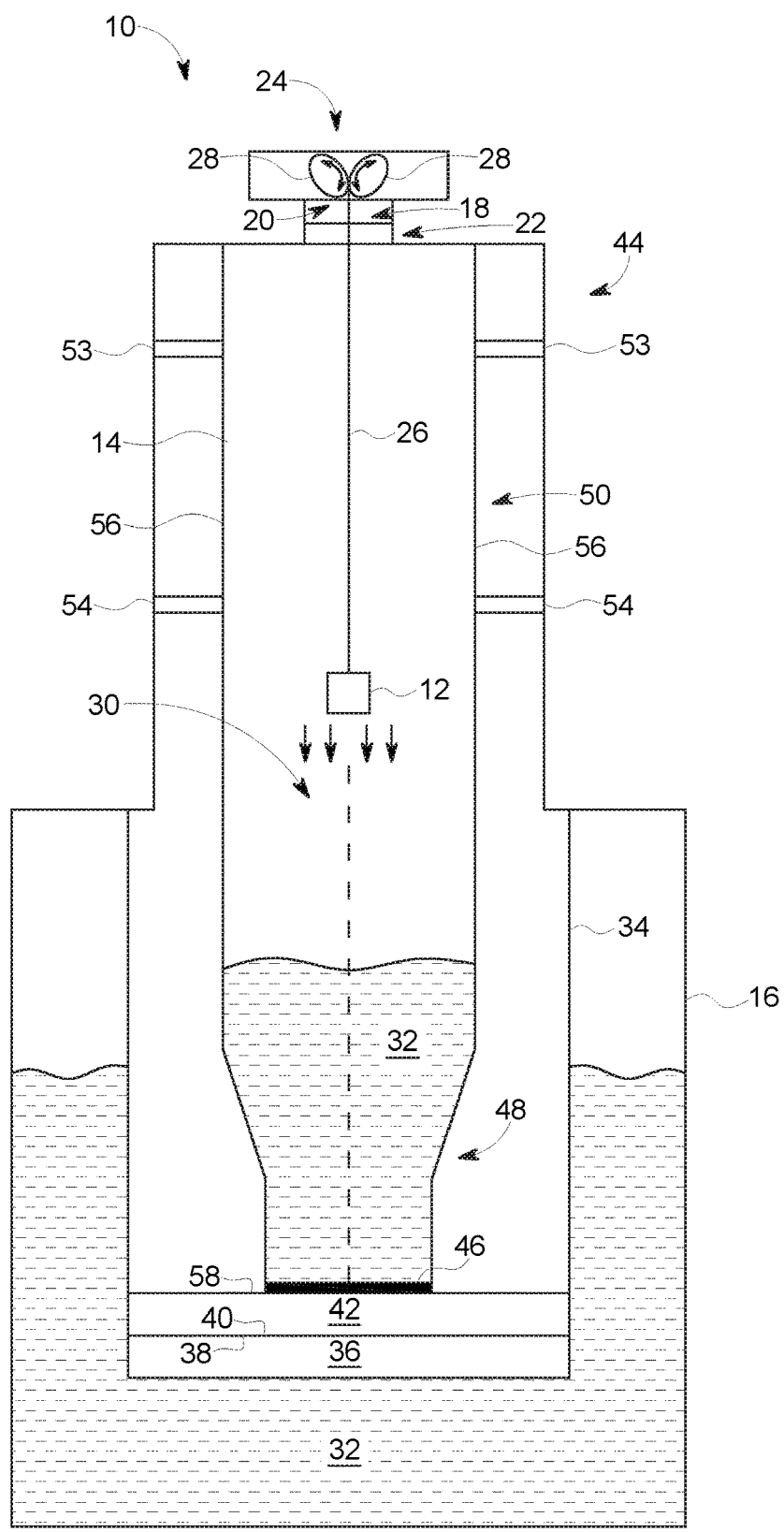
FIG. 2 is a schematic diagram of the cooling system of FIG. 1 that includes a sample that is being lowered towards a sample pot of the cooling system, in accordance with present embodiments.

With the discussion of FIG. 1 in mind, FIGS. 2-6 illustrate a progression of ice forming within the removable sample sleeve 14 and de-icing occurring via actuation of the thermal switch 42. More specifically, FIG. 2 is schematic diagram of the cooling system 10 illustrating the sample 12 being lowered toward the sample pot 34 for cooling. As described above, the sample 12 may be moved via the positioning system 24.

Figure 3:
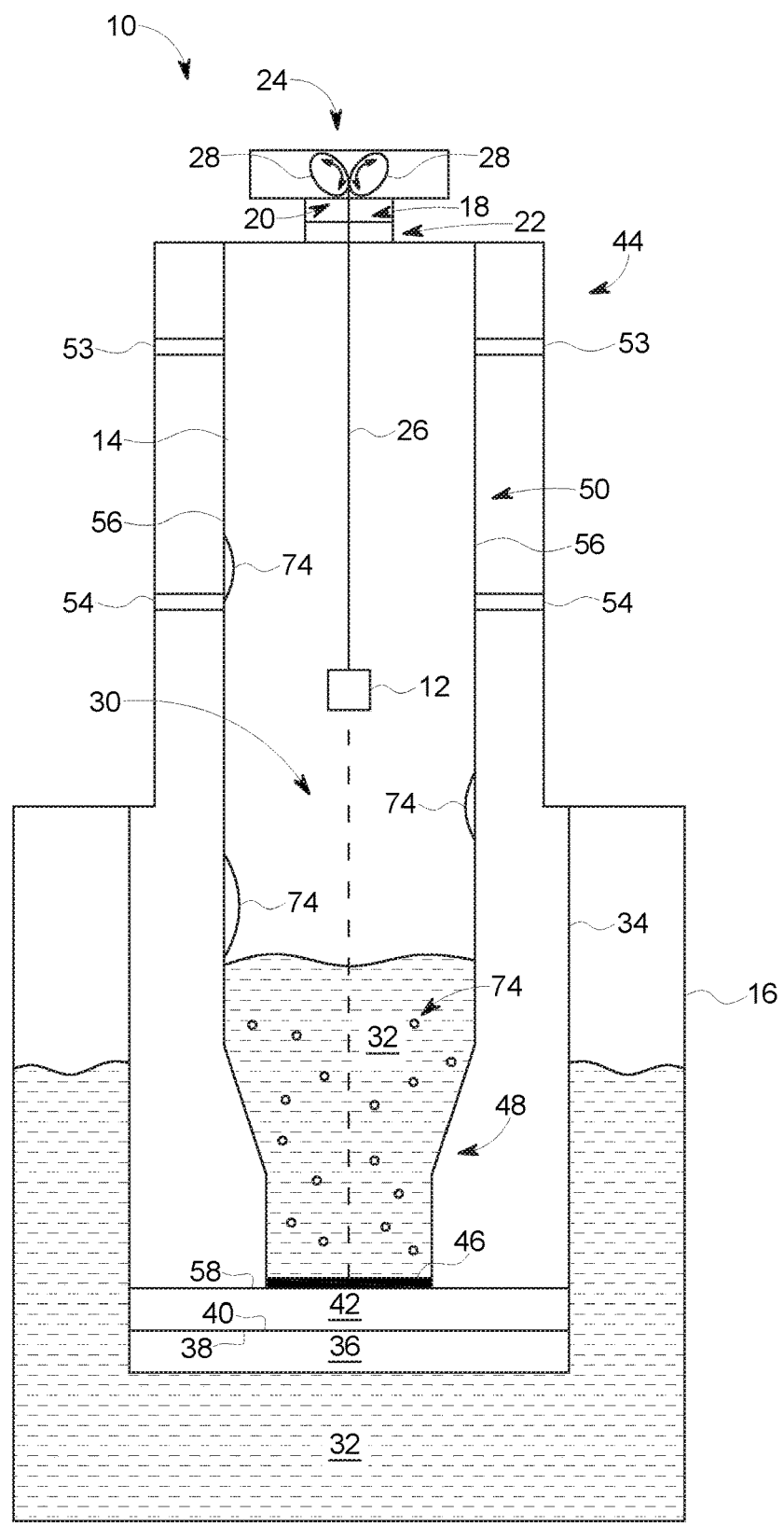
FIG. 3 is a schematic diagram of the cooling system of FIG. 1, in accordance with present embodiments, in which ice has formed.

FIG. 3 is a schematic diagram of the cooling system 10 with ice 74 that has formed. In certain situations, for example due to unforeseen circumstances, while the sample 12 is in the cooling system 10, the container of the sample 12 may break, causing a release of water from the container, causing ice to form. However, as described above, the ice 74 may form for other reasons. As described above, the formation of ice may be restricted to occurring within the removable sample sleeve 14. As such, the ice 74 is only located within the removable sample sleeve 14.

Figure 4:
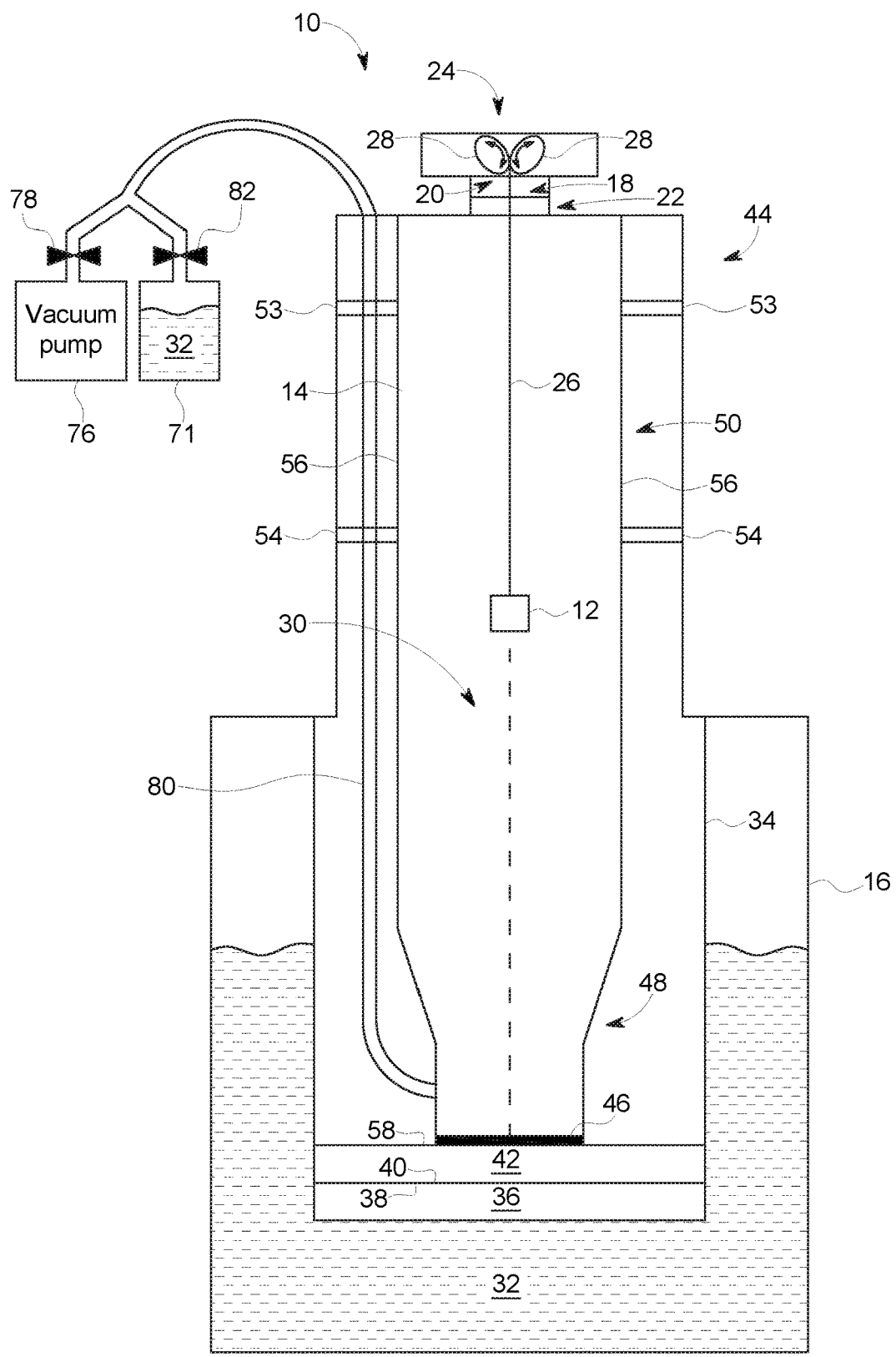
FIG. 4 is a schematic diagram of the cooling system of FIG. 1, in accordance with present embodiments.

FIG. 4 is a schematic diagram of the cooling system 10 in which the thermal switch 42 has been actuated (e.g., via user input or controller 62 input), causing heat to spread from the top surface 58 of the thermal switch to the bottom surface 46 of the lower portion 48 of the removable sample sleeve 14, which may continue to spread along the walls 56 of the removable sample sleeve 14. As described above, the thermal switch 42 may cause the bottom surface 46 of the removable sample sleeve 14 to warm, for example to room temperature. As also illustrated, the increase in temperature may cause some or all of the cryogenic fluid 32 within the removable sample sleeve to become gaseous. For example, the cryogenic fluid 32 may include liquid helium, and the liquid helium may evaporate as a result of the heating. The evaporated cryogenic fluid 32 and any contaminants in the removable sample sleeve 14 may be removed, and more cryogenic fluid 32 may be added to the removable sleeve 14. For example, the evaporated cryogenic fluid 32 and contaminants may be removed via a vacuum pump 76 by opening a valve 78 on a tube 80 that is connected to the removable sample sleeve 14. Additionally, cryogenic fluid 32 may be added to the removable sample sleeve 14 by opening a valve 82 associated with the external source 71 of cryogenic fluid 32. While the tube 80 is illustrated as being coupled to the lower portion 48 of the removable sample sleeve 14, the tube may be coupled to other locations along the removable sample sleeve 14 in other embodiments (e.g., the body portion 50 or the upper portion 51).

Figure 5:
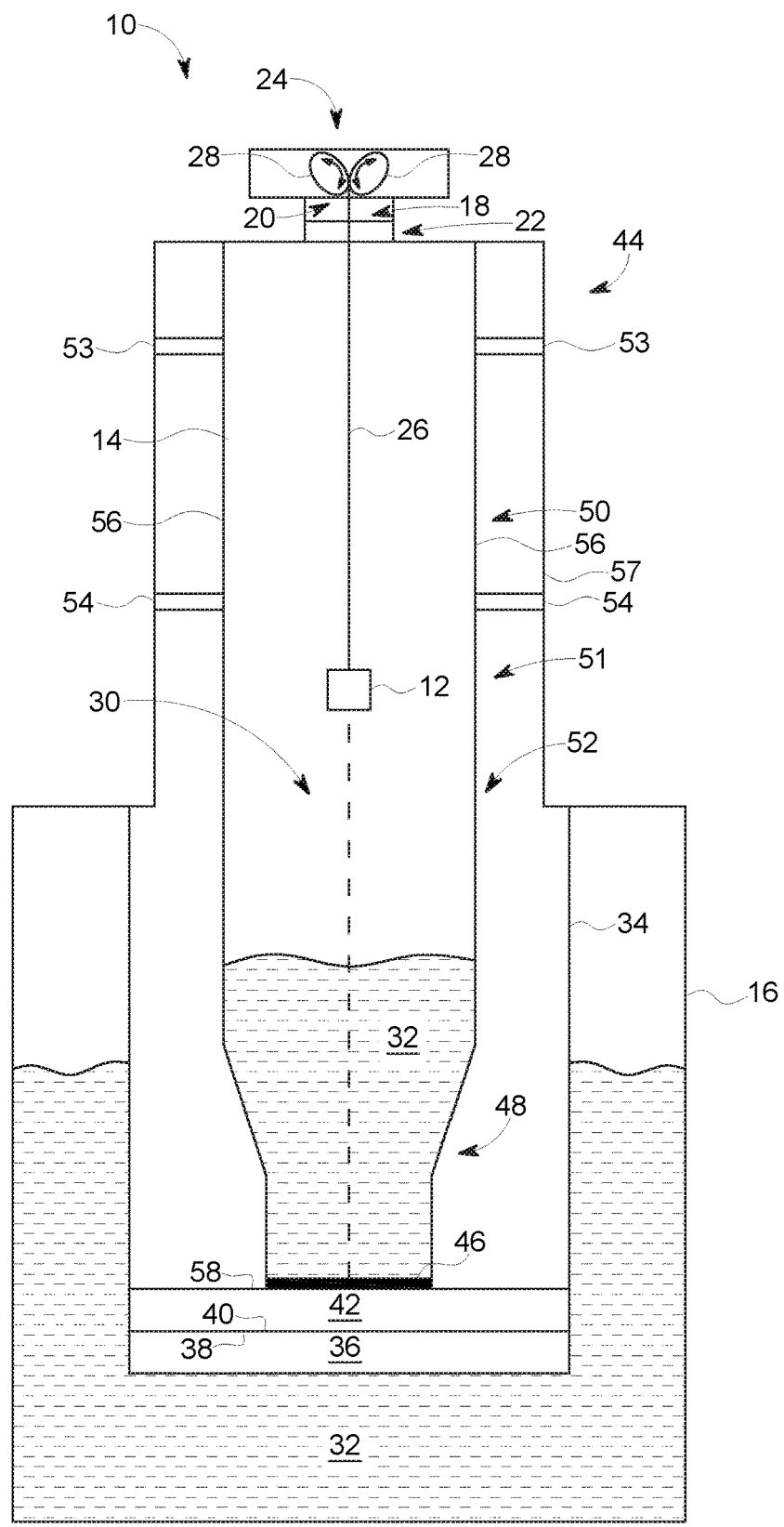
FIG. 5 is a schematic diagram of the cooling system of FIG. 1 in which a thermal switch of the cooling system has been actuated, in accordance with present embodiments.

Continuing with the drawings, FIG. 5 is a schematic illustration of the cooling system 10 after the thermal switch 42 has been deactivated. For instance, at a time after heating has commenced, such as when de-icing has finished or when a temperature suitable for causing de-icing is reached, the thermal switch 42 may be deactivated. That is, heat may cease to be generated via the thermal switch 42. The cooling system 10 may then being to be cooled such that a suitable temperature in the sample pot 34 is obtained (e.g., about 0.75 Kelvin to 0.95 Kelvin). Moreover, as illustrated, as the temperature of the removable sample sleeve 14 decreases, the cryogenic fluid 32 may return to a liquid state. However, as discussed above, it should be noted that more cryogenic fluid 32 may also be added to the removable sample sleeve 14.

Figure 6:
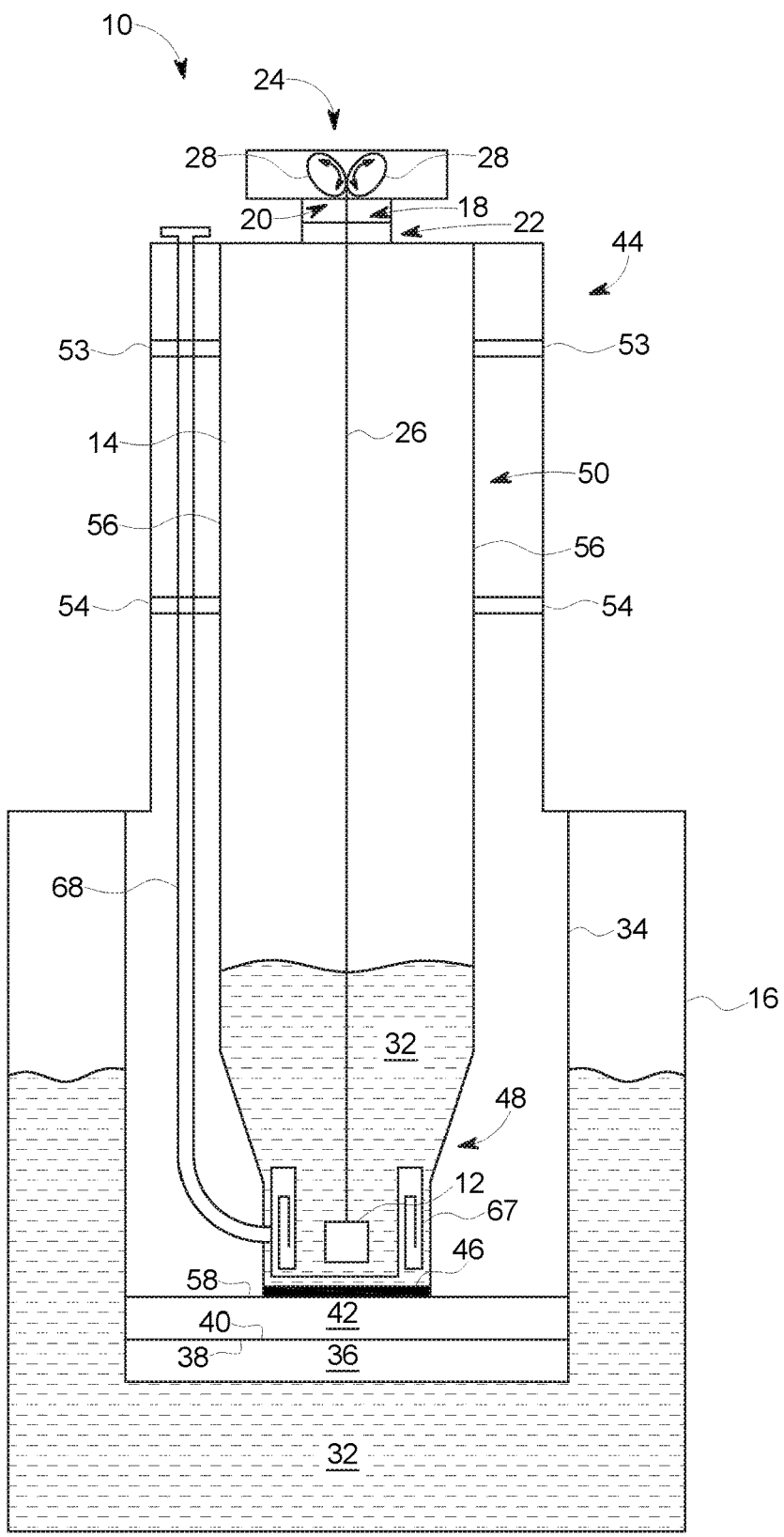
FIG. 6 is a schematic diagram of the cooling system of FIG. 1 that includes a sample cooled via cryogenic fluid, in accordance with present embodiments.

Turning now to FIG. 6, which is another schematic diagram of the cooling system 10, after the temperature within the sample pot 34 has reached a temperature suitable for cooling the sample 12, the sample 12 may be cooled. After the sample 12 has been suitably cooled and positioned inside the nuclear magnetic resonance coil 67, microwaves may be directed onto the sample 12 through the waveguide 68 to perform DNP.

Figure 7:
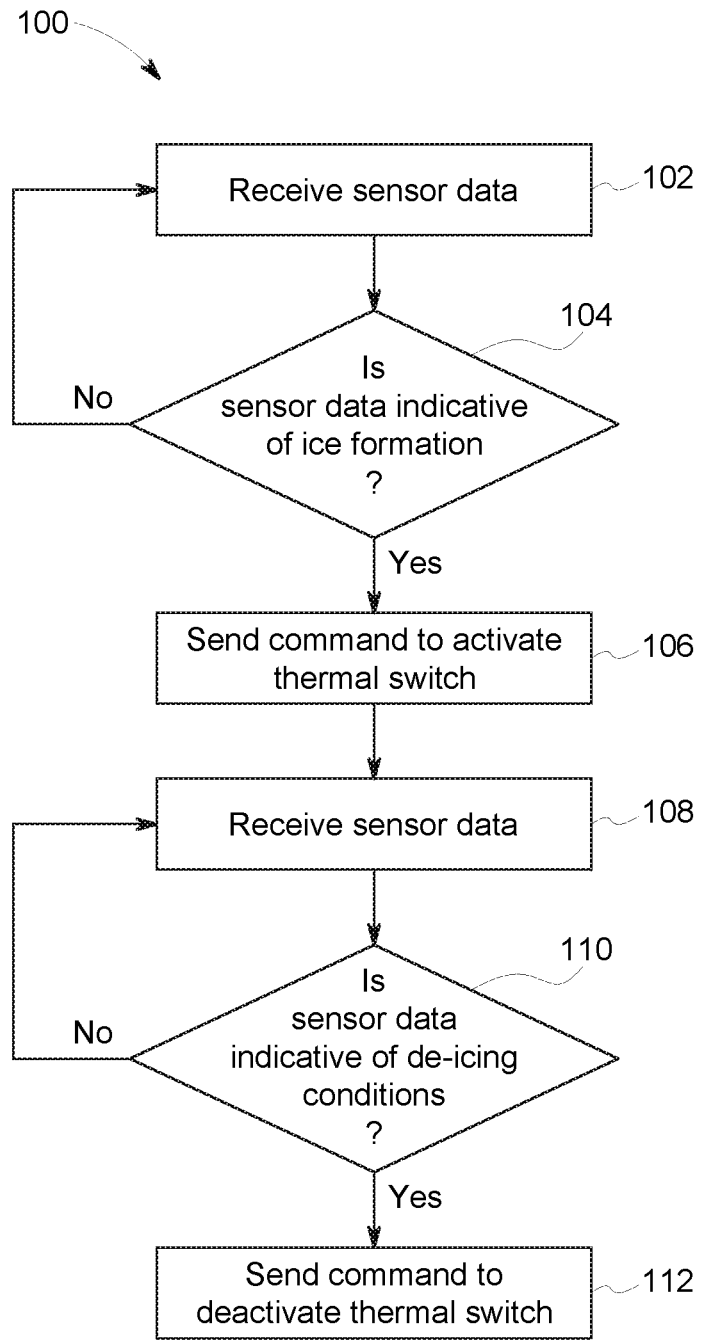
FIG. 7 is a flow chart of a method for de-icing the cooling system of FIG. 1, in accordance with present embodiments.

FIG. 7 is a flow chart of a method 100 for de-icing the cooling system 10 using the thermal switch 42, for example as performed by the controller 62. At block 102, the controller 62 may receive data from the sensors 60. As described above, the data from the sensors 62 may pertain to various properties of the cooling system 10 such as a temperature, pressure, and/or a status of the sample 12 (e.g., location within the cooling system 10 and/or whether the sample has broken).

At block 104, the controller 62 may determine whether the sensor data is indicative of ice formation (e.g., presence of ice 74). As described above, the controller 62 includes processor 64 and memory 66. The processor 64 may execute instructions stored on the memory 66, and may access reference values for various parameters and compare the actual values for the parameters to the reference values to determine whether the sensor data is indicative of ice formation r other occurrences. For instance, the controller 12 may determine that the sensor data is indicative of the sample 12 breaking. As another example, the controller 12 may determine that data associated with detected temperatures and/or pressures may be indicative of ice formation. If the controller 62 determines that the sensor data is not indicative of ice formation, the controller 62 may continue to receive sensor data as described above with regard to block 102.

However, if the controller 62 determines in the affirmative that the sensor data is indicative of ice formation, at block 106, the controller 62 may send a command to actuate the thermal switch 42. In other words, when the sensor data is indicative of ice formation, the controller 42 may send a command that causes the thermal switch 42 to heat the bottom surface 46 of the removable sample sleeve 14.

At block 108, the controller 62 may receive sensor data, and at block 110 the controller 62 may determine whether the sensor data is indicative of de-icing conditions. For instance, the controller 62 may determine whether the sensor data is indicative of temperature and/or pressure conditions within the cooling system 10 that would cause the ice 74 to melt. For example, and as explained above, actuation of the thermal switch 42 may cause the bottom surface 46 of the removable sample sleeve 14 to be heated (e.g., to standard temperature). The controller 62 may determine that data indicative of the bottom surface 46 being room temperature, as well as data indicative of other temperatures and/or conditions, may be indicative of de-icing conditions having been achieved. As another example, the controller 62 may determine whether the sensor data is indicative of the bottom surface 46 or another portion of the removable sample sleeve 14 (e.g., the walls 56) having a temperature that is equal to or greater than a predetermined temperature value. If the controller 62 determines that the sensor data is not indicative of de-icing conditions, the controller 62 may continue to collect sensor data (block 108).

If the controller 62 determines that the sensor data is indicative of de-icing conditions, at block 112, the controller 62 may send a command to deactivate the thermal switch 42. That is, the controller 62 may send a command that causes the thermal switch 42 to cease heating the removable sample sleeve 14.

Figure 8:
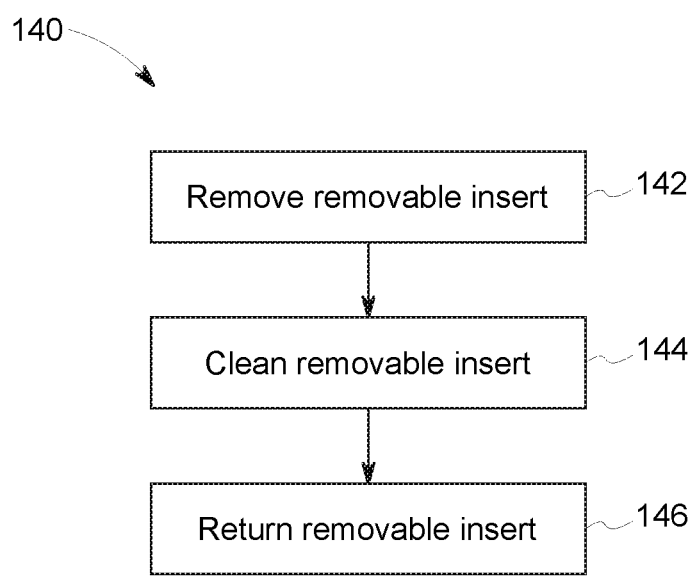
FIG. 8 is a flow chart of a method for de-icing the cooling system of FIG. 1, in accordance with present embodiments.

FIG. 8 is a flow chart of a method 140 for de-icing the cooling system 10. At block 142, the removable sample sleeve 14 may be removed from the cooling system 10. For instance, an operator or the controller 62 may determine that ice is present or that conditions within the cooling system 10 are such that ice may form or may have formed and remove the removable sample sleeve 14 in response to such a determination.

At block 144, the removable sample sleeve 14 may be cleaned. Cleaning the removable sample sleeve 14 may include performing an activity that causes ice or other foreign material to be removed from the removable sample sleeve 14. For example, cleaning the removable sample sleeve 14 may include physically removing the ice 74 or other foreign material from the removable sample sleeve 14.

At block 146, the removable sample sleeve 14 may be returned to the cooling system 10. The removable sample sleeve 146 may be secured into place via the first set of links 53 and the second set of link 54.

Figure 9:
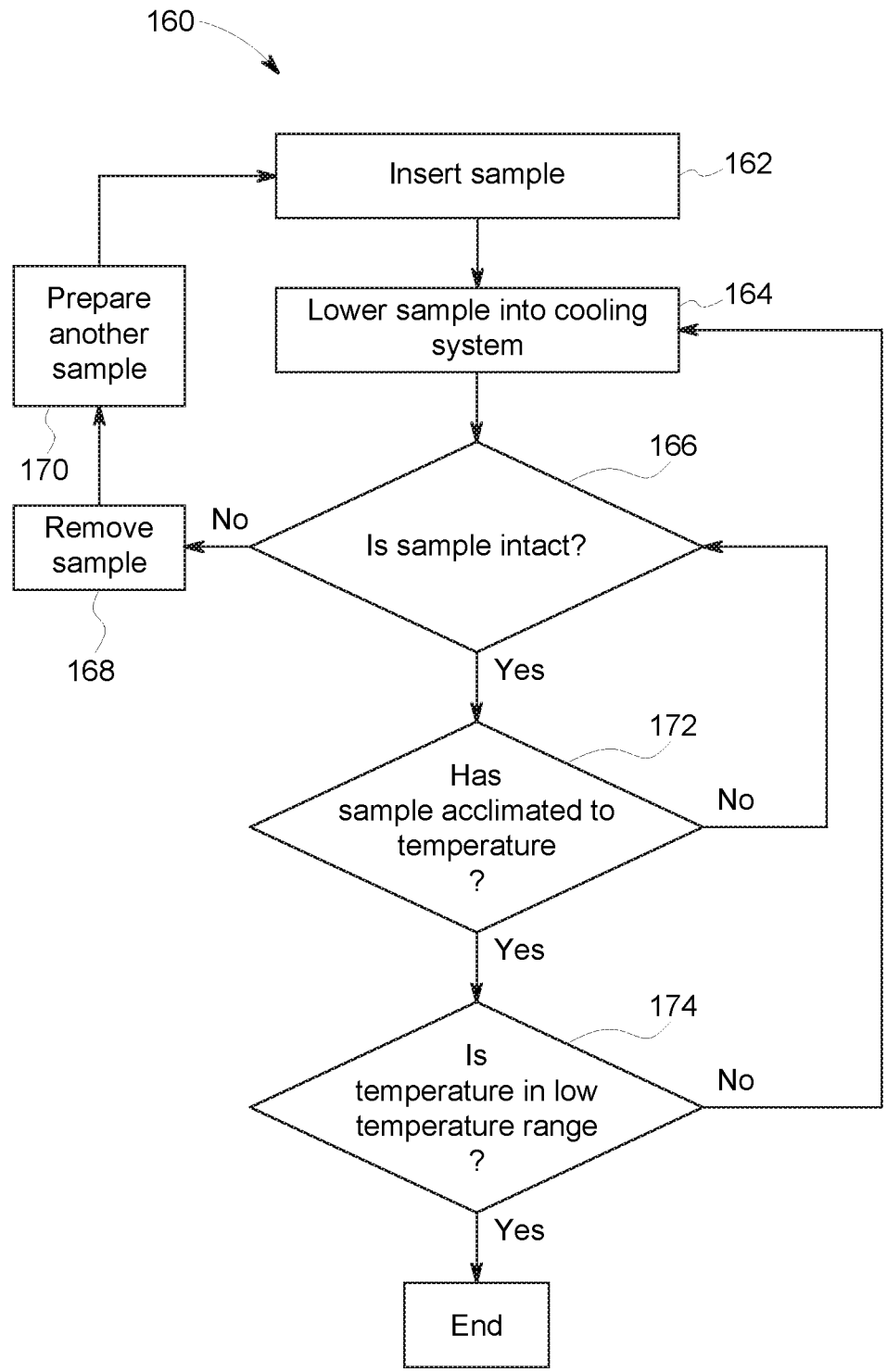
FIG. 9 is a flow chart of a method for cooling samples in the cooling system FIG. 1, in accordance with present embodiments.

FIG. 9 is a flow chart of a method 160 for cooling the sample 12 using the cooling system 10. The method 160 may be performed, for example, totally or in part by the controller 62 in combination with features of the cooling system 10 described herein. At block 162, the sample 12 is inserted into the cooling system 10. For example, the sample 12 may be placed within the airlock chamber 18. Insertion in accordance with block 162 may also involve some amount of depressurization to facilitate cooling of the sample 12.

At block 164, the sample 12 may be lowered within the cooling system 10. More specifically, the sample 12 may be lowered within the removable sample sleeve 14. For instance, the sample 12 may be lowered past the gate valve 22 and within the removable sample sleeve 14 via the positioning system 24. The sample 12 may be lowered varying amounts within the cooling system 10. For example, the sample may first be lowered to an area between the gate valve 22 and the first set of links 53.

Generally, the sample 12 may be lowered at a rate that allows for acclimation to the temperatures within the area of the removable sample sleeve 14 that the sample 12 occupies. Continuing from block 164, at block 166, whether the sample 12 is intact may be determined. While shown as occurring after the acts represented by block 164, it should be noted that the controller 62 may substantially continuously monitor the status of the sample 12 and perform appropriate determinations relating thereto. In other words, the acts (e.g., query) represented by block 166 may be performed substantially continuously, at intervals, and so forth.

In response to determining that the sample 12 is not intact, at block 168, the sample 12 may be removed, and, at block 170, a new sample may be prepared. The new sample may then be inserted into the cooling system for cooling as represented at block 162.

In response to determining that the sample is intact, at block 172, it may be further determined whether the sample 12 has acclimated to the temperature within the cooling system 10. For instance, the sample 12 may have been lowered to an area within the cooling system that has a temperature of about 30 K, and whether the sample has acclimated to such a temperature may be determined. Determining whether the sample 12 has acclimated to a temperature may include determining whether the sample 12 has a temperature that is within a range of temperatures or within a certain percentage of the temperature at a given point within the cooling system 10. Moreover, determining whether the sample 12 has acclimated to the temperature may be based on a period of time. For instance, if the sample 12 has been at a certain position within the cooling system 10 for a certain period of time, it may be determined whether the sample 12 has acclimated to the temperature of the cooling system 10. If the sample 12 has not acclimated to the temperature within the cooling system 10, it may be determined whether the sample 12 is still intact (block 166). As one example, the controller 62 may monitor the temperature of the sample 12 over time to determine whether the temperature has equilibrated, whether it is continuing to change, and/or whether it is changing at a rate indicative of temperature acclimation. In such embodiments, the temperature of the sample 12 may be determined to have equilibrated if it does not change by a certain amount over a period of time.

In response to determining that the sample 12 has acclimated to the temperature within the cooling system 10, at block 174, it may be determined whether the sample 12 is located in a portion of the cooling system 10 that has a temperature in a low temperature range. For example, the low temperature range may include a range of temperatures (e.g., between about 4 K and about 0.7 K) suitable to cool the sample 12 to a desired temperature. More specifically, the low temperature range may be about 0.75 K to 0.95, which may correspond to the temperature within the sample pot 34 or the lower portion 48 of the removable sample sleeve 14. If the sample 12 is not located within a portion of the cooling system 10 that has a temperature in the low temperature range, the sample 12 may be lowered more (block 164).

If the sample 12 is located in a portion of the cooling system 10 that has a temperature in the lower temperature range, the sample 12 may be sufficiently cooled. The sample 12 may subsequently be utilized in or subjected to other processes associated with systems having the cooling system 10. For example, once cooled, the sample 12 may be subjected to dynamic nuclear polarization, followed by magnetic spectroscopy or imaging processes.

Technical effects of the present disclosure include a removable sample sleeve 14 that is configured to collect ice 74 that formed within the cooling system 10. More specifically, the removable sample sleeve 14 prohibits the formation of ice outside of the removable sample sleeve 14. That is, ice 74 is limited to forming within the removable sample sleeve 14. Additionally, the removable sample sleeve 14 includes a thermal switch 14 that may heat the removable sample sleeve 14 to perform de-icing. Furthermore, technical effects of the present disclosure also include methods for de-icing the cooling system 10 in a manner that allows for de-icing to be completed in less than twenty-four hours.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A cooling system associated with a dynamic nuclear polarization system, wherein the cooling system is configured to cool a sample to a temperature suitable for dynamic nuclear polarization to be carried out on the sample while the sample is in the cooling system, and wherein the cooling system comprises:
    a cryogenic chamber comprising a cryogenic fluid;
    a sample pot positioned within the cryogenic chamber, the sample pot being at least partially surrounded by the cryogenic fluid;
    a removable sample sleeve inserted into the sample pot such that a lower portion of the removable sample sleeve is positioned in the sample port and an upper portion of the removable sample sleeve protrudes out of the sample pot, and wherein the removable sample sleeve is configured to define a sample path for the sample within the cryogenic chamber that is isolated from other parts of the cooling system.

2. The cooling system of claim 1, wherein the removable sample sleeve is configured to contain the formation of ice to within the sample path.

3. The cooling system of claim 1, wherein the cryogenic fluid comprises liquid helium.

4. The cooling system of claim 1, comprising a thermal switch attached to the lower portion of the removable sample sleeve, wherein the thermal switch is configured to be positioned between the sample pot and a bottom surface of the lower portion of the removable sample sleeve.

5. The cooling system of claim 4, comprising a cold plate positioned in the sample pot and configured to act as a thermal interface between the thermal switch and the sample pot.

6. The cooling system of claim 4, wherein the thermal switch is configured to heat the removable sample sleeve to a temperature sufficient to de-ice the sample path while the removable sample sleeve is positioned within the sample pot.

7. The cooling system of claim 4, comprising:
    a plurality of sensors configured to collect data regarding the cooling system; and
    a controller comprising a processor and memory, wherein the controller is configured to receive the data from the plurality of sensors and cause actuation of the thermal switch based on the data.

8. The cooling system of claim 1, wherein the removable sleeve is configured to receive a volume of cryogenic fluid.

9. The cooling system of claim 1, comprising a positioning system configured to move the sample through the sample path defined by the removable sample sleeve.

10. The cooling system of claim 1, comprising a plurality of links configured to secure the removable sample sleeve within the cooling system.

11. A removable sample sleeve configured to be disposed within a cooling system of a dynamic nuclear polarization system, and collect ice that forms within the cooling system, wherein the removable sample sleeve comprises:
    an upper portion configured to be disposed within a portion of the cooling system outside of a sample pot of the cooling system;
    a lower portion configured to be disposed within the sample pot, wherein the lower portion comprises a thermal switch configured to warm the lower portion; and
    a body portion configured to be disposed both within and outside of the sample pot.

12. The removable sample sleeve of claim 11, wherein the removable sample sleeve is made from a metal or metal alloy.

13. The removable sample sleeve of claim 11, wherein the thermal switch is configured to prevent ice from forming within areas of the cooling system outside of the removable sample sleeve.

14. The removable sample sleeve of claim 11, wherein the thermal insert is configured to be removed from the bottom surface of the removable sample sleeve.

15. A controller-executable method of de-icing a removable insert sleeve of a cooling system, the method comprising:
    receiving a first set of sensor data from one or more sensors configured to collect data regarding the cooling system, wherein the cooling system is configured to cool a sample, wherein the cooling system comprises a removable sample sleeve configured to collect ice that forms within the cooling system, wherein the removable sample sleeve comprises a thermal insert configured to directly heat a bottom surface of the removable sample sleeve;

determining whether the first set of sensor data is indicative of ice formation in the cooling system;

sending a command to actuate a thermal switch when the first set of sensor data is indicative of ice formation in the cooling system;

receiving a second set of sensor data from the one or more sensors;

determining whether the second set of sensor data is indicative of de-icing conditions; and sending a command to deactivate the thermal switch when the second set of sensor data is indicative of de-icing conditions.

16. The method of claim 15, wherein the first set of data is associated with a detected temperature, pressure, or a status of the sample.

17. The method of claim 15, wherein the thermal switch is configured to heat the bottom surface of the removable sample sleeve to at least 290 Kelvin.

18. The method of claim 15, wherein at least one of the one or more sensors is positioned on a wall of the removable sample sleeve.

19. The method of claim 15, wherein determining whether the second set of sensor data is indicative of de-icing conditions comprises determining whether a temperature of the bottom surface is equal to or greater than a predetermined temperature value.

* * * * *